US008609119B2

(12) United States Patent
Tarasi et al.

(10) Patent No.: US 8,609,119 B2
(45) Date of Patent: Dec. 17, 2013

(54) ACTIVE AGENT DELIVERY AND/OR ODOR RETENTIVE COMPOSITION AND METHODS OF USE THEREOF

(75) Inventors: Raymond J. Tarasi, Pittsburgh, PA (US); Gary W. Dalrymple, Allison Park, PA (US); Peter Pugliese, Bernville, PA (US); Steven M. Pugliese, Bernville, PA (US)

(73) Assignee: UNIREM, Inc., Pittsburgh, PA (US)

( * ) Notice: Subject to any disclaimer, the term of this patent is extended or adjusted under 35 U.S.C. 154(b) by 0 days.

(21) Appl. No.: 13/546,369

(22) Filed: Jul. 11, 2012

(65) Prior Publication Data

US 2012/0276180 A1    Nov. 1, 2012

Related U.S. Application Data

(60) Division of application No. 12/491,903, filed on Jun. 25, 2009, now Pat. No. 8,236,333, which is a continuation-in-part of application No. 12/090,927, filed as application No. PCT/US2006/041162 on Oct. 19, 2006, now abandoned.

(51) Int. Cl.
*A61K 9/50* (2006.01)
*A61K 47/44* (2006.01)
*A61Q 5/00* (2006.01)
*A61Q 19/00* (2006.01)

(52) U.S. Cl.
USPC ........... 424/401; 424/451; 424/502; 514/787; 510/119; 510/130

(58) Field of Classification Search
USPC ........ 435/262.5; 424/401, 451, 502; 514/785, 514/787; 510/119, 130
See application file for complete search history.

(56) References Cited

U.S. PATENT DOCUMENTS

| | | |
|---|---|---|
| 3,732,162 A | 5/1973 | McCoy at al. |
| 3,959,127 A | 5/1976 | Bartha et al. |
| 4,196,851 A | 4/1980 | Davis |
| 4,292,326 A | 9/1981 | Nazzaro-Porro |
| 4,386,104 A | 5/1983 | Nazzaro-Porro |
| 4,885,282 A | 12/1989 | Thornfeldt |
| 5,112,495 A | 5/1992 | Bartha et al. |
| 5,348,803 A | 9/1994 | Schlaemus et al. |
| 5,385,943 A | 1/1995 | Nazzaro-Porro |
| 5,395,535 A | 3/1995 | Pinckard |
| 5,406,019 A | 4/1995 | Dean |
| 5,451,325 A | 9/1995 | Herkenberg |
| 5,492,881 A | 2/1996 | Diamond |
| 5,589,194 A * | 12/1996 | Tsuei et al. .................... 424/497 |
| 5,674,504 A | 10/1997 | Kauffmann |
| 5,727,902 A | 3/1998 | Brown |
| 5,807,724 A | 9/1998 | Resnick |
| 5,910,455 A | 6/1999 | Maddern et al. |
| 5,954,868 A | 9/1999 | Felix et al. |
| 5,980,644 A | 11/1999 | Ivanov |
| 6,045,813 A * | 4/2000 | Ferguson et al. ............. 424/401 |
| 6,303,109 B1 * | 10/2001 | Foerster et al. ............ 424/70.31 |
| 6,398,960 B1 | 6/2002 | Borden et al. |
| 6,428,775 B1 | 8/2002 | Habif et al. |
| 6,447,789 B1 | 9/2002 | Banks |
| 6,531,160 B2 * | 3/2003 | Biatry et al. .................. 424/490 |
| 6,541,439 B1 | 4/2003 | Zabarylo |
| 6,572,892 B1 * | 6/2003 | Ioulalen et al. ............... 424/489 |
| 6,683,037 B2 | 1/2004 | Mondin |
| 6,699,390 B1 | 3/2004 | Griffin et al. |
| 7,115,282 B2 | 10/2006 | Shefer et al. |
| 7,166,221 B1 | 1/2007 | Young et al. |
| 7,223,423 B2 | 5/2007 | Hwa |
| 7,241,941 B1 | 7/2007 | Horejsi et al. |
| 7,329,403 B2 | 2/2008 | Chuah et al. |
| 7,351,418 B2 | 4/2008 | Collin |
| 7,413,745 B2 | 8/2008 | Gotou et al. |
| 7,485,609 B2 | 2/2009 | Reddy et al. |
| 7,511,003 B2 | 3/2009 | Focht et al. |
| 7,524,807 B2 | 4/2009 | Clapp et al. |
| 7,632,489 B2 | 12/2009 | Wyatt et al. |
| 7,879,344 B2 | 2/2011 | Feldkamp et al. |
| 2004/0057921 A1 | 3/2004 | Walsh |
| 2004/0221503 A1 | 11/2004 | Murphy et al. |
| 2005/0079145 A1 | 4/2005 | Constantinides et al. |
| 2006/0260633 A1 | 11/2006 | Wyatt et al. |

FOREIGN PATENT DOCUMENTS

| | | | |
|---|---|---|---|
| JP | 10212500 A | * | 8/1998 |
| WO | 2007047992 | | 4/2007 |

OTHER PUBLICATIONS

English Language machine translation of JP 10-212500 (Aug. 11, 1998) pp. 1-9.*
"Processing Beeswax"; http://www.bindaree.com.au/hints/brief1.htm; Aug. 5, 1999; Brief No. 1; Version 1.
"PRP: The Proven Solution for Cleaning Up Oil Spills"; NASA Spinoff; 2006.
"Oil Spills—A Fact Sheet"; http://www.awma.org/education/oilspills.htm; revision May 1, 2000.
"A Hope for Oil SPill Bioremediation"; http://www.sciencedaily.com/releases/2005/05/050517063708.htm; May 17, 2005.
"NRT Science and Technology Committee—Fact Sheet: Bioremediation in Oil Spill Response"; May 2000.
"Product Data Sheet 88-583-1 Partially Hydrogenated Specifications"; www.admworld.com, (Jan. 2002).

* cited by examiner

*Primary Examiner* — William H Beisner
(74) *Attorney, Agent, or Firm* — The Webb Law Firm

(57) ABSTRACT

An active agent delivery and/or odor retentive composition including a surfactant and wax spheres formed from at least one of beeswax and soy wax and methods of use thereof. The composition is particularly useful in the cosmetics and medical industry for delivering/carrying a particular ingredient to one's skin, scalp or hair; for absorbing odor causing materials, such as fuel byproducts from a skin surface; and/or for providing exfoliating properties to the skin. The delivery system/carrying system is also useful in binding to certain nutritional materials, such as vitamins, minerals, antioxidants, and the like for ingestion and release into the body.

12 Claims, No Drawings

ACTIVE AGENT DELIVERY AND/OR ODOR RETENTIVE COMPOSITION AND METHODS OF USE THEREOF

CROSS REFERENCE TO RELATED APPLICATIONS

This application claims priority as a divisional of U.S. patent application Ser. No. 12/491,903, filed on Jun. 25, 2009, now U.S. Pat. No. 8,236,333 which is a continuation-in-part to U.S. patent application Ser. No. 12/090,927, filed on Apr. 21, 2008, now abandoned which is the national stage of International Application No. PCT/US2006/041162, filed on Oct. 19, 2006, the contents of each of which are expressly incorporated herein by reference.

BACKGROUND OF THE INVENTION

1. Field of the Invention

The invention relates generally to uses of and compositions comprising wax spheres comprising at least one of soy wax and beeswax. The invention is particularly useful in the cosmetic, nutritional and/or medical industry.

2. Description of Related Art

Cleansers and topical application materials for treating skin and/or scalp conditions, removing contaminants, and/or providing exfoliating properties to the skin/scalp are common in the cosmetic and medical industry. U.S. Pat. No. 6,447,789 shows an example of one type of facial cleanser having a formulation comprising a phosphate salt that provides exfoliating properties and sequestering properties for removing harmful metals from the skin. Other examples of cleansing formulations are taught by U.S. Pat. Nos. 4,292,326; 4,386,104; 5,385,943; and 4,885,282. A major drawback for many of these types of cleansers or topical formulations is that they can deleteriously react with one's skin causing skin irritations, rashes, redness, crusting, and the like.

Carrying mediums for ingestion within the body to deliver an active ingredient or nutritional supplement such as vitamins, minerals, nutrients, antioxidants and the like are also known. Some types of nutritional supplements are difficult to bind with these carrying mediums and/or are not water soluble. As such, the preparation of these nutritional supplements for ingestion into the body, is difficult and costly. Further, these carrying mediums can deleteriously react with the body and/or result in undesirable side effects.

There is a need in the art for a delivery method using a delivery/carrying medium which is relatively benign and unreactive with the body tissues, inexpensive to produce and easy to combine with other components.

Accordingly, there is a present need for a system and composition for delivering an active ingredient comprised of a cost-effective, readily available material, which, can be applied either topically or internally to a body, which is relatively benign in nature having little to no side effects.

SUMMARY OF THE INVENTION

The present invention provides an active ingredient delivery and/or odor retentive composition that is particularly useful in the cosmetics and medical industry for delivering/carrying a particular ingredient to one's skin, scalp or hair; for absorbing odor causing materials, such as fuel byproducts from a skin surface; and/or for providing exfoliating properties to the skin. The delivery system/carrying system is also useful in binding to certain nutritional materials, such as vitamins, minerals, antioxidants and the like for ingestion and release into the body. The present invention also provides a composition and methods of use thereof which address the problems associated with prior art.

According to one aspect, the invention is directed to a composition for the topical application to skin and/or hair or for ingestion into a body. The composition comprises a surfactant and wax spheres comprised of at least one of beeswax and soy wax. The wax spheres are typically hollow spheres having an average diameter of between 0.20 and 1,000 micrometers. According to one embodiment, the wax spheres are present in an amount of between 2 and 8% by weight based on the total weight of the composition. The wax spheres can include a lipid-soluble compound absorbed therein. This lipid-soluble compound can be a vitamin or vitamin precursor.

According to another aspect, the invention is directed to a wax sphere comprised of at least one of beeswax and soy wax, wherein the wax sphere comprises a lipid-soluble compound absorbed therein. The wax sphere can be a hollow sphere having an average diameter of between 0.20 and 1,000 micrometers and the lipid-soluble compound is a lipid-soluble vitamin or vitamin precursor. According to one embodiment, the lipid-soluble compound is a tocopherol compound. According to another embodiment, the lipid-soluble compound is a nutritional supplement.

According to yet another aspect, the invention is directed to a method of cleaning or treating the skin or hair comprising the step of topically applying to the skin or hair a composition comprising wax spheres comprised of at least one of beeswax and soy wax. The method further includes the step of massaging the composition against the skin or hair so as to rupture the wax spheres or to cause the wax spheres to contact and absorb lipid-soluble compounds from the skin and/or hair. This can further include the step of massaging the composition against the skin so as to exfoliate the surface of the skin. According to one embodiment, the wax spheres are hollow and can have a lipid-soluble substance absorbed therein.

These and other features and characteristics of the present invention, as well as the methods of operation and functions of the related elements of structures and the combination of parts and economies of manufacture, will become more apparent upon consideration of the following description with reference to the accompanying examples. It is to be expressly understood, however, that the examples are for the purpose of description only and are not intended as a definition of the limits of the invention.

DESCRIPTION OF THE INVENTION

The present invention provides wax spheres comprised of soy wax and/or beeswax and the use of those wax spheres to deliver to the body and/or remove from the body lipid-soluble substances. The present invention also provides compositions including these wax spheres.

As used herein, the term "lipid" means any fat-soluble molecule, including, but not limited to, fats, oils, waxes, cholesterol, sterols, fat-soluble vitamins, monoglycerides, diglycerides, and phospholipids. The term "lipid-soluble" refers to a compound's lipophilicity, or ability to dissolve in fats, oils, lipids, and non-polar solvents.

The wax spheres are comprised of soy wax, beeswax, or a combination thereof. Generally, the wax spheres are hollow and, in one embodiment, the spheres have an external diameter in a range between about 0.20 and 1,000 micrometers and, in another embodiment, the spheres have an external diameter between about 5 to 50 micrometers. Optionally, the spheres may contain suitable chemical- and/or petrochemical-degrading microbes, such as various species of *Pseudomonas* or *Bacillus*, in concentrations of about $5 \times 10^6$ microbes per 200 pounds of wax.

Either the hollow or bacteria-filled form of the wax spheres can be manufactured by conventional technology known to those skilled in the art. Several prior art devices are suitable for manufacturing the hollow spheres. Suitable devices include the Komfeld Rotary Reactor, a device developed by NASA (see NASA Tech Briefs, MFS-28214, "Rotary Reactor Makes Large Latex Particles"); or through utilization of other encapsulating devices or processes, such as the Vanderhoff Rotary Reactor (also a NASA technology), by microshell manufacturers, e.g., KMS Industries of Ann Arbor, Mich., Picro-Pak, Inc. of NY, or Insulated Technologies Corp. of Philadelphia, Pa. The spheres may be made by the method described in U.S. Pat. No. 5,807,724, which is incorporated herein by reference.

A method is provided for manufacturing wax spheres comprising soy wax. The method comprises several steps. The first step involves heating soy wax to a temperature above 135° F. and pressurizing the tank to at least 340 psi, wherein the first tank is connected to a brass housing. Optionally, an amount of beeswax can be heated along with the soy wax, creating a homogenous wax mixture. Preferably, the amount of soy wax in the wax mixture is between 50% and 99% of the total weight of the mixture and ideally the amount of soy wax is between 60% and 80%. The second step involves providing a second tank filled with one of the group selected from air, water and solution containing live microbes and nutrients, and pressurizing the tank to at least 300 psi, wherein the second tank is connected to the brass housing. The third step involves spraying the soy wax or wax mixture and one of the group selected from air, water and solution containing live microbes and nutrients through a hypodermic needle with an external orifice connected to the brass housing, wherein the soy wax or wax mixture is sprayed through the external orifice having an internal diameter of at least 12 thousandths of an inch, and wherein the one of the group selected from air, water and solution containing live microbes and nutrients is sprayed through the hypodermic needle having an internal diameter of at least 5 thousandths of an inch. The fourth step involves cooling the sprayed soy wax or wax mixture to below 135° F. to form spheres comprising soy wax or wax mixture. The spheres may also be made by other methods known to those skilled in the art.

Suitable forms of soy wax can be obtained from any commercially available source. For example, suitable soy wax pellets produced from partially hydrogenated soybean oil are sold by Archer Daniels Midland Co. (ADM), identified by product number 88-583-1. The Product Data Sheet providing partially hydrogenated specifications for soy wax product 88-583-1 is incorporated herein by reference. Other suitable forms of soy wax are known to one skilled in the art. Natural beeswax is available commercially through distributors and is usually sold in 15 to 25 pound slabs. Beeswax spheres are described in U.S. Pat. No. 6,699,390, the contents of which are expressly incorporated herein by reference. The economic advantages of substituting some or all of the beeswax for soy wax in the hollow spheres are based upon commercially available soy wax pellets, which are derived from the plentiful source of soy beans. Soy wax pellets sell at a market price that is sufficiently less in comparison to the market price of beeswax.

Wax spheres are non-toxic and relatively inexpensive. In addition, the geometric characteristics, such as the small size and spherical configuration, provide a large exterior surface area relative to the volume and weight of the spheres. The large surface area provides a large area through which lipid-soluble substances can be absorbed by and released from the wax spheres.

In one non-limiting embodiment, a composition suitable for application to the skin and/or hair and having an amount of the above-described wax spheres dispersed throughout is provided. In some non-limiting applications, the composition can be used to remove lipid-soluble substances, such as dirt and oil, from the skin and/or hair. In some non-limiting applications, the composition can additionally (or alternatively) be used to deliver a lipid-soluble substance that has been absorbed in the wax sphere to the skin and/or hair.

The wax spheres are suspended or dispersed in the composition but not completely dissolved within. While in some embodiments, the wax spheres may be evenly or at least substantially evenly distributed throughout the composition, the invention is not so limited. Because the wax spheres may be denser than other components of the composition, the wax spheres may congregate at a particular position relative to the remaining portions of the composition. For instance, the wax spheres may aggregate near the bottom of a container housing the composition when the container is in a vertically upright position. Agitation of the composition will allow the wax spheres to disperse throughout.

A composition including the wax spheres described herein can be used to clean the skin and/or hair to remove unwanted organic, lipid-soluble compounds therefrom. It has been found that the wax spheres described herein can absorb, and thus remove, a lipid-soluble substance from the skin and/or hair. Built-up organic substances in the skin and hair can cause an offensive odor and increase the toxicity level in the skin. For instance, volatile organic compounds, such as those derived from petroleum sources like gasoline, diesel fuel, and machine oils, can rapidly penetrate the outer layer of the skin or hair and can produce both lasting odors and skin irritation. It has been found that the lipid-absorbing activity of the wax spheres can act to draw the organic compounds away from the skin and hair where they can be absorbed by the wax spheres.

A composition including the wax spheres can also provide an exfoliating effect when applied to the skin. Exfoliation is commonly defined as the process of removing dead skin cells from the body. Exfoliation can be achieved through the mechanical scrubbing of the skin with an abrasive material such as a sponge or loofah. When a composition having the wax spheres described herein is applied to the skin, the wax spheres can act as an exfoliating agent by providing abrasion when the composition is rubbed on the body. The exfoliating force of the wax spheres may be much less harsh than many available exfoliation techniques, such as those mechanical abrasive materials mentioned above.

The wax spheres can make up between about 0.5 and about 25 wt %, such as between 2 and 8 wt %, based on the total weight of the composition. In some non-limiting embodiments, the composition includes about 5 wt % wax spheres based on the total weight of the composition.

The composition may also include one or more surfactant materials. Any suitable surfactant that does not detrimentally interfere or react with the wax spheres or the other components in the composition can be used. This includes, but is not limited to, amphoteric or zwitterionic surfactants, anionic surfactants, nonionic surfactants, and/or cationic surfactants. Some non-limiting examples of suitable surfactants include sodium methyl-2-sulfolaurate, disodium sulfolaurate, cetrimonium chloride, cocoamidopropyl betaine, and sodium lauryl sulfoacetate. Other suitable surfactants include those disclosed in U.S. Pat. Nos. 7,485,609 and 7,524,807, the contents of which are expressly incorporated herein by reference.

As would be recognized by those skilled in the art, the surfactant can represent the major component of the composition, with the amount of the surfactant ranging from about 20 up to about 95 wt % based on the total weight of the composition, though compositions containing less surfactant are also envisioned.

The composition may optionally include other ingredients and additives commonly used in creating skin and/or hair cleaning formulations as would be appreciated by one skilled in the art. Some non-limiting examples of additional ingredients include fragrances, moisturizing agents (including, but not limited to, emollients and humectants), dyes, organosilicon compounds, preservatives, and thickeners, which can each independently be provided in amounts as necessary for consumer acceptance. Some non-limiting examples of suitable thickening agents include xanthan gum, xanthan gum brine tolerant, hydroxypropyl cellulose, hydroxyethyl cellulose, cellulose esters, carrageenans, sodium alginate, cetyl alcohol, carbopol, guar gum, and gum acacia. Non-limiting examples of suitable moisturizing agents include, for example, urea, glycerin, sorbitol, xylitol, PCA, amino acids, and mineral oils. Non-limiting examples of suitable organosilicon compounds, which can be used to make hair shiny or slippery, include polydimethylsiloxanes (dimethicones). Non-limiting examples of suitable preservatives include $C_1$-$C_4$ parabens (e.g., methylparaben, ethylparaben), capryl glycol, hexylene glycol, and methylisothiazolones. Water, such as deionized water, may also be included in the composition in amounts necessary to accomplish the desired consistency, viscosity or other properties of the composition.

In some embodiments, the composition can be in the form of an oil-in-water or water-in-oil emulsion and include, in addition to the wax spheres, thickeners, such as those listed above, emulsifying agents (which may be a surfactant) including glycerols, and/or polysorbates, preservatives, fragrances, water, etc.

The compositions can be prepared by adding each of the components of the composition in a vessel and agitating the vessel to distribute the components. In one embodiment, water can be added to a final mixing vessel and propeller agitation can be started. If more than one surfactant material is being added to the composition, the surfactants can be mixed together in a separate vessel and then added to the water. In a separate vessel, the wax spheres and other additives, such as fragrances and moisturizing agents, can be mixed and a preservative can be added. The individual mixtures can then be combined in a final mixing vessel and the composition can be agitated, such as through propeller agitation or other mechanical mixing, to distribute the components of the composition.

As mentioned above, a composition including the wax spheres can be used to deliver to the skin and/or hair a lipid-soluble substance. For instance, it has been found that the wax spheres can be prepared to have a lipid-soluble substance absorbed therein. Upon contacting a lipid surface, such as the surface of the skin or hair, a wax sphere can release or transfer the lipid-soluble substance from the area having a high concentration of the substance (i.e., the sphere) to the lipid surface (i.e. the skin or hair surface), which initially has a lower concentration of the substance. It is believed that the transfer properties can be approximated by Fick's laws of diffusion. Different release or transfer rates can be achieved by changing the size of the spheres, and thus the surface area, and the loading amount of the lipid-soluble substance.

In some non-limiting embodiments, the wax spheres described above can have absorbed therein a lipid-soluble vitamin or vitamin precursor compound, and preferably compounds which exhibit vitamin activity beneficial to the skin and/or hair. The term "vitamin precursor" includes compounds that can be converted into a vitamin by the body, and is sometimes referred to in the art as a "vitamer". Some non-limiting examples of useful compounds include vitamin E or precursors thereof, such as tocols and tocotrienols, and preferably tocopherol-based compounds such as tocopheryl acetate, vitamin B-12 or precursors thereof, such as cyanocobalamin, hydroxocobalamin, methylcobalamin, or 5-deoxyadenosylcobalamin, vitamin B-3 or precursors thereof, such as niacinamide and nicotinic acid, vitamin A or precursors thereof, such as axerophtol or retinoic acid, vitamin D, vitamin $D_3$, vitamin K, and the like, including precursors thereof. The amount of each vitamin that is included in the composition can be adapted based to specific needs and depends, at least in part, on the quantity and loading capability of the particular wax spheres used in a particular composition. For example, a high concentration of vitamin E may be preferred for compositions directed to consumers having particularly damaged skin or hair.

Wax spheres having a lipid-soluble substance absorbed therein can be produced by mechanically mixing together the lipid-soluble substance and the wax spheres. By adjusting the size of the wax spheres, the total load (i.e., amount) of the lipid-soluble substance absorbed by the spheres can be adjusted. In some instances, it may be preferred to first solubilize the lipid-soluble substance in oil. Once the lipid-soluble substance is solubilized, wax spheres can be contacted with the solution, allowing the wax spheres to absorb the solution, including the dissolved lipid-soluble substance. Non-limiting examples of suitable oils that may be used to solubilize a vitamin compound include soy bean oil and rice bran oil, though any vegetable or animal oil that can dissolve the subject lipid-soluble substance may potentially be used. To facilitate the dissolving of the lipid-soluble substance in the oil, the oil may be heated as needed. Many common vitamin compounds, such as tocopherol, are provided in a liquid form, and do not need to be solubilized prior to coming in contact with the wax spheres.

In some non-limiting embodiments, the wax spheres may have absorbed therein a chemical exfoliate or keratolytic agent. Keratolytic agents, when contacted with the skin, can aid in the loosening or shedding of the skin. Potentially useful chemical exfoliates include acid-based, organic exfoliates such as salicylic acid. The chemical exfoliates can be combined with the wax spheres according to the procedures outlined above with respect to the vitamin compounds, including a procedure in which the exfoliate is first solubilized in an oil-based solution, such as soy bean oil, and then taken up by the wax spheres.

Other lipid-soluble chemicals and compounds useful in the treatment of the hair or skin can be similarly employed. Wax spheres including more than one lipid-soluble compound may also be used.

Methods are provided for using the above-described compositions to treat or clean skin or hair. In one embodiment, the compositions can be topically applied to the skin to remove from the skin unwanted organic, lipid-soluble compounds that may be on or below the surface of the skin. If it is desired to achieve an exfoliating effect from the use of the composition, the method may include gently rubbing or massaging the composition against the surface of the skin to allow the wax spheres to gently exfoliate the skin and remove dead skin cells. Inclusion of a wax sphere having a chemical exfoliate absorbed therein can also be used to increase the exfoliating effect.

If the wax spheres of the composition have absorbed therein a lipid-soluble substance, the method may include a step of massaging the composition against the skin so as to rupture the wax spheres, thereby releasing the lipid-soluble substance onto the skin more rapidly. In another embodiment, the compositions can be applied to the hair. After the composition has been applied to the hair, the method may include a step of rubbing or massaging the composition against the scalp.

In some non-limiting embodiments, the wax spheres can also be used as a nutritional supplement that can be ingested by the body. Many nutritional supplements, such as certain antioxidants and vitamins, are not water-soluble. For example, the antioxidant ellagic acid is not water-soluble, making it difficult to incorporate it into food products. Ellagic acid can, however, be incorporated, or absorbed, into the wax spheres described herein according to the methods described. Once wax spheres having the nutritional supplement absorbed therein have been prepared, they can then be directly ingested as an ingestible or incorporated into a food product, such as a vitamin bar, for consumption. Some potential advantages of incorporating nutritional supplements in this manner is ease of preparation, even distribution, cold preparation, that is, no heat needed, and protection from oxidation.

The following examples are intended to further illustrate the invention and are not meant to be limiting.

EXAMPLES

Example 1

A non-limiting example of a cleansing composition having wax spheres is shown below in Table 1:

TABLE 1

| Ingredient | Amount (by weight %) |
| --- | --- |
| mixture of sodium methyl-2-sulfolaurate, disodium sulfolaurate, and sodium lauryl sulfoacetate | 50.00 |
| Deionized water | 28.30 |
| Cocoamidopropyl betaine | 9.60 |
| Beeswax spheres | 5.00 |
| Cetrimonium chloride | 4.00 |
| Glycerin | 1.50 |
| Preservative | 0.80 |
| Xanthan gum | 0.50 |
| Fragrance (Raw honey) | 0.30 |

The composition of Table 1 was prepared by adding water to a final mixing vessel and beginning propeller agitation. A premix of the glycerin and xanthan gum was prepared in a separate vessel and then added to the water phase. The surfactants were combined in a separate vessel and added to the water phase. In a separate vessel, the cetrimonium chloride, wax spheres and fragrance were mixed, and then a preservative was added. The pH level was measured to be 5.0.

Example 2

An oil-in-water emulsion composition including wax spheres in which a vitamin E compound is absorbed therein is described. All weight percents are based on the total weight of the final composition. The wax spheres having the vitamin compound can be produced by contacting wax spheres, such as those described herein, with tocopheryl acetate or tocopherol, which are present as a liquid. The quantity of wax spheres used can vary depending on the harshness desired for the composition. If a harsh cleanser (in terms of mechanical abrasiveness) is desired, about 5 wt % wax spheres should be used. If a less harsh composition is desired, 1 wt % wax spheres can be used. Amounts between 1 and 5 wt % can be employed as desired. The amount of vitamin compound depends, in part, on the quantity and loading capabilities of the wax spheres, but, in one example, about 1 wt % tocopheryl acetate or tocopherol is used.

The composition can further include between 1 and 5 wt % cetyl alcohol as a thickener, between 5 and 7 wt % glycerol monostearate SE as an emulsifying agent, about 1 wt % polysorbate 20 (TWEEN 20) as an emulsifying agent, between about 0.1 and 0.2 wt % fragrance, and a combination of methylparaben and butylparaben as a preservative at a total amount of about 0.2 wt %. A quantity sufficient ("q.s.") amount of deionized water is added to bring the composition to the desired weight.

This formulation allows the wax spheres to remain in suspension and to be topically applied in a uniform layer over the skin surface. As the skin is also a lipid layer, the vitamin E will be attracted to the lipid layer of the skin by mass diffusion. Rubbing the spheres causes the vitamin E to be delivered in a more rapid manner as the spheres are crushed, releasing the vitamin E more quickly.

Example 3

In another non-limiting example, a composition including wax spheres having a chemical exfoliate absorbed therein is provided. The details of the composition are shown below in Table 2. This example shows an exfoliating beeswax scrub for calloused areas. This formula contains a combination of gentle exfoliation wax spheres that are impregnated with salicylic acid. This results in a dual action of a chemical keratolytic action on the callous along with a gentle mechanical abrasive action (from the wax spheres) as well. The net effect is to remove the callous gradually, painlessly and safely.

TABLE 2

| Ingredient | Amount (by weight %) |
| --- | --- |
| mixture of disodium 2 sulfolaurate and sodium lauryl sulfoacetate | 45.30 |
| Deionized water | 28.00 |
| Cocoamidopropyl betaine | 9.60 |
| Complex of beeswax spheres and salicylic acid solubilized in soy bean oil | 10.00 |
| Cetrimonium chloride | 4.00 |
| Glycerin | 1.50 |
| Preservative (Capryl glycol, hexylene glycol, and Methylisothiazolone) | 0.80 |
| Xanthan gum | 0.50 |
| Fragrance (Raw honey) | 0.30 |

The preparation of salicylic acid-containing beeswax spheres is achieved by heating 100 grams of soy bean oil to 50° C. and adding 10 grams of salicylic acid (as a powder) to the heated oil to dissolve the acid therein. Then 100 grams of the beeswax spheres are contacted with the oil solution. The beeswax spheres absorb the oil and the salicylic acid. The thus prepared beeswax spheres include a chemical exfoliate (i.e.

the salicylic acid) as an integral part of the physical component. In other words, the salicylic acid is an integral component of the beeswax spheres.

The formula in Table 2 was prepared as follows. The water was added to the final mixing vessel. The xanthan gum and glycerin were premixed in a separate vessel and then added to the water phase. In another vessel, the surfactants were combined and blended and then added to the water phase. In another vessel, the cetrimonium chloride, fragrance and beeswax/salicylic acid complex were blended and then added to the water phase. The preservative was then added to the water phase, the mixture was blended and the pH was adjusted to 5.0, as needed.

Example 4

Another non-limiting example of a composition according to the present invention is shown below in Table 3. This example shows a gentle, all-body scrub for removal of devitalized tissue. Deionized water is listed twice in Table 3, for reasons that will be explained below.

TABLE 3

| Ingredient | Amount (by weight %) |
|---|---|
| Deionized water | 47.58 |
| Carbopol Ultrez 20[1] | 0.90 |
| Sodium Hydroxide (18% by volume) | 0.12 |
| Deionized water (combined with HiCare) | 6.00 |
| HiCare 1000[2] | 0.10 |
| Tetrasodium EDTA | 0.10 |
| Colonial SLES-2[3] | 34.00 |
| Sodium Cocoamphoacetate | 5.00 |
| Dimethicone 200[4] | 0.70 |
| Wax spheres having a 60-40 blend of soy and bees wax | 5.00 |
| Phenonip[5] | 0.50 |

[1] thickening agent available from Lubrizol.
[2] cationic guar gum available from Rhone-Poulenc Rorer.
[3] sodium laureth sulfate surfactant available from Colonial Chemicals, Inc.
[4] a polydimethylsiloxane having a viscosity of 200 centistokes.
[5] a preservative available from Clariant Functional Chemicals.

The formula in Table 3 was prepared as follows. Water was added to the final mixing vessel (representing the first "Deionized water" entry in Table 3). A gel mixture was prepared by solubilizing the Carbopol with the sodium hydroxide. The HiCare was prepared in water (representing the second "Deionized water" entry in Table 3) and EDTA was added. The remaining ingredients were mixed and added to the final mixing vessel. The HiCare and Carbopol were then added and the mixture was blended well. The formula was then ready for packaging.

Example 5

A non-limiting example of a vitamin candy bar composition comprising wax spheres having absorbed therein a nutritional supplement is provided. Preparation of the candy bar begins with a base of nut butter or organic dates. A variety of proteins such as whey protein, rice protein, organic nuts and/or flaxseed can then be added. Next, natural sweeteners such as cherries, raisins, cranberries, etc, can be added in the appropriate amounts corresponding to the desired sweetness level. Various grains and seasonings such as, for example, cocoa powder or cinnamon can be added.

An oil-soluble vitamin compound, such as a vitamin A, D and/or E compound, is mixed with rice bran oil to solubilize the vitamin. An equal volume of wax spheres can be contacted with the vitamin solution and the wax spheres absorb the solution. The wax spheres, with the vitamin solution absorbed therein, can then added to the base candy bar composition. The composition is blended and then pressed into a bar shape for packaging.

The formulation allows nutritional supplements to remain bound until ingested into the body. Once ingested the supplement is released. This system is especially useful for the ingestion of some nutritional supplements that are not water-soluble and difficult to incorporate into food products. This system also allows for an even distribution of the nutritional supplement and is easy to prepare.

While the present invention is satisfied by embodiments in many different forms, there is described herein in detail the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

The invention claimed is:

1. A method of cleaning or treating the skin or hair comprising the steps of topically applying to the skin or hair a composition comprising a surfactant in an amount between 20 and 95% by weight based on the total weight of the composition and wax spheres comprised of at least one of beeswax and soy wax, wherein at least a first portion of the wax spheres are hollow spheres adapted to absorb organic, lipid-soluble substances from the skin and/or hair; and massaging the composition against the skin or hair so as to cause the wax spheres to absorb lipid-soluble compounds from the skin and/or hair.

2. The method of claim 1, wherein the method further includes the step of massaging the composition against the skin so as to exfoliate the surface of the skin.

3. The method of claim 1, wherein a second portion of the wax spheres comprise an organic exfoliate absorbed therein.

4. The method of claim 3, wherein the organic exfoliate is salicylic acid.

5. The method of claim 3, wherein the method further includes the step of massaging the composition against the skin and/or hair so as to rupture the wax spheres of the second portion, and thereby deliver the organic exfoliate to the skin and/or hair.

6. The method of claim 1, wherein a second portion of the wax spheres have a lipid-soluble substance absorbed therein.

7. The method of claim 6, wherein the lipid-soluble substance is a vitamin or vitamin precursor.

8. The method of claim 7, wherein the method further includes the step of massaging the composition against the skin or hair so as to rupture the wax spheres of the second portion and thereby deliver the vitamin or vitamin precursor to the skin and/or hair.

9. The method of claim 6, wherein the lipid-soluble substance is a tocopherol compound.

10. The method of claim 9, wherein the method further includes the step of massaging the composition against the skin or hair so as to rupture the wax spheres of the second portion and thereby deliver the tocopherol compound to the skin and/or hair.

11. The method of claim 6, wherein the method further includes the step of massaging the composition against the skin or hair so as to rupture the wax spheres of the second portion and thereby deliver the lipid-soluble substance to the skin and/or hair.

12. The method of claim 1, wherein the wax spheres comprise beeswax.

* * * * *